United States Patent [19]

Démarcq

[11] 4,083,899
[45] Apr. 11, 1978

[54] ACCELERATED PROCESS OF ALCOHOLYSIS OR PHENOLYSIS OF PHOSPORUS PENTASULFIDE

[75] Inventor: Michel Démarcq, Lyon, France

[73] Assignee: Produits Chimiques Ugine Kuhlmann, Paris, France

[21] Appl. No.: 659,096

[22] Filed: Feb. 18, 1976

Related U.S. Application Data

[63] Continuation of Ser. No. 363,128, May 23, 1973, abandoned.

[30] Foreign Application Priority Data

Jun. 7, 1972 France .............................. 72.20487

[51] Int. Cl.$^2$ ............................................ C07F 9/165
[52] U.S. Cl. .................................................... 260/981
[58] Field of Search ....................................... 260/981

[56] References Cited
U.S. PATENT DOCUMENTS 3,848,032  4/1974  Le Suer et al. ...................... 260/981

*Primary Examiner*—Anton H. Sutto
*Attorney, Agent, or Firm*—Pennie & Edmonds

[57] ABSTRACT

New process of alcoholysis or phenolysis of $P_2S_5$ in the presence of a catalyst having one of the following structures:

(A) $X(Y)_nNQQ'$ having 1 to 20 C-atoms and 1 to 10 heteroatoms O, S, N or P; X, Q and Q' are hydrogen or univalent hydrocarbon radicals or form rings together; Y is O, S or a bivalent nitrogen or phosphorus radical; $n = 0$ or 1.

(B) $(X')_m(Y)_nN=Z$ having 1 to 20 C-atoms and 1 to 10 heteroatoms O, S, N or P; $m = 0$ or 1; X' has the same meaning as X or is equivalent to —N=Z or —NQQ'; Z is O, S or a bivalent carbon or hydrocarbon radical, which may form a ring with X'.

(C) $X(Y)_n$—C≡N with 0 to 20 C-atoms and 1 to 6 heteroatoms O, S, N or P.

Application to the preparation of dialkyl- or diaryldithiophosphoric acids used to manufacture phosphorus insecticides, dopes for lubricants, ore flotation agents etc.

2 Claims, No Drawings

ACCELERATED PROCESS OF ALCOHOLYSIS OR PHENOLYSIS OF PHOSPORUS PENTASULFIDE

This is a continuation of application Ser. No. 363,128, filed May 23, 1973, now abandoned.

BACKGROUND OF THE INVENTION

I. Field of the Invention

This invention relates to the use of new catalysts to accelerate the reaction of phosphorus pentasulfide with alcohols or phenols.

II. Description of the Prior Art

Phosphorus pentasulfide is widely used as a raw material in the manufacture of O,O-dialkyl- or O,O-diaryl-dithiophosphoric acids, which have many uses; e.g. in the formulation of anti-oxidation and anticorrosion "dopes" for motor oils, as ore flotation agents or as intermediaries for the synthesis of phosphorus insecticides.

The alcoholysis and phenolysis of phosphorus pentasulfide are generally described by the following reaction:

$$P_2S_5 + 4 ROH \rightarrow 2 (RO)_2P(S)SH + H_2S \uparrow \qquad I$$

Actually, as various authors have shown (K. Moedritzer and J. R. van Wazer, J. Inorg. Nucl. Chem. 25 (1963), 683–690; A. E. Lippman, J. Org. Chem. 31 (1966), 471–473; L. Nebbia and V. Bellotti, La Chimica e l'Industria 52 (1970)(4), 369–371), the main product $(RO)_2P(S)SH$ is always accompanied by minor quantities of other phosphorus esters: for example, $(RO)_2P(S)H$, $(RO)_2P(S)SR$, $(RO)_3PS$, $(RO)_2POSH$, $RO—PS(OH)_2$, $RO—PS(SH)(OH)$, $(RO)_2P(S)—S—(S)P(OR)_2$, $(RO)_2P(S)—SS—(S)P(OR)_2$ even when purified phosphorus pentasulfide is used.

In addition, separation of a small quantity of sulfur can be observed, especially with commercial phosphorus pentasulfides, even when elementary analysis of the latter does not indicate the presence of sulfur in stiochiometric excess.

The speed with which an alcohol or a phenol reacts with phosphorus pentasulfide under given conditions may vary over a wide range depending upon the origin of the latter. The speed of this reaction is of great commercial importance because of its effect of the efficiency of the process plants in which dialkyl- and diaryldithiophosphoric acids are produced. The rate of this reaction is described by a "reactivity" index which is evaluated by means of a calorimetric alcoholysis test, the alcohol used usually being isopropanol. This index varies little with speed of agitation or the mesh size of the powdered $P_2S_5$ reagent, but does depend greatly on the crystalline structure of the phosphorus pentasulfide.

According to P. Bencze (Revue de l'Institut Francais du Petrole XXV (1970), No. 5, 647–676), the alcoholysis of phosphorus pentasulfide takes place according to the following process:

(1) Rapid physical dissolution of the $P_2S_5$ in the alcohol, followed by, (2) Slower chemical reaction of the dissolved $P_2S_5$ with the alcohol.

The first step, being very rapid, tends in effect to keep the liquid alcohol saturated with $P_2S_5$. The over-all speed of the reaction, as governed by the slow step (2), may be represented by the equation.

$$v = \frac{-d(ROH)}{dt} = k(ROH)(P_2S_5), \qquad II$$

where (ROH) represents the alcohol concentration (which decreases with time) and $(P_2S_5)$ represents the concentration of dissolved $P_2S_5$ (which is substantially constant). For a particular sample of $P_2S_5$, Bencze determined the value of $(P_2S_5)$ in isobutanol at 40° to be 0.15%.

Analysis of commercial phosphorus pentasulfides by X-ray diffraction shows that they generally consist of a mixture of an "abnormal" (amorphous or microcrystalline) phase and a normal, well crystallized, phase. The former is metastable and more soluble in solvents than the latter. According to Formula II, therefore, the metastable variety reacts faster with alcohols than the crystalline variety. The reactivity of a phosphorus pentasulfide sample will thus be in direct proportion to the amount of abnormal phase material present.

This "abnormal" phase, the structure of which has not been established, is perhaps identical with the highly active variety isolated by H. Vincent (thesis defended Feb. 19, 1969, before the Faculty of Sciences of the University of Lyon, France) via vacuum sublimation of $P_2S_5$ heated to 200°–220° with condensation of the vapors on a wall cooled with liquid air.

It is also well known that commercial phosphorus pentasulfides when subjected to abrupt cooling or "quenching" from the molten state contain more abnormal phase and are more reactive than those allowed to cool slowly (see K. Moedritzer and J. R. van Wazer, op. cit. supra).

U.S. Pat. No. 3,023,086 states that the time taken to traverse the interval from 280° to 260° C. (pure $P_2S_5$ melts at 288°) is critical. The reactivity increases for example from 1 to 10 when this period is reduced from 2 min. 30 sec. to 0.125 sec.

However, such a quenching operation presents formidable technical problems on a commercial scale. U.S. Pat. No. 3,282,653 for example describes a conveyor belt system having three temperature zones serving to cool the phosphorus sulfide sequentially from 400° to 250° C.; development of such equipment on a commercial scale would seem a rather difficult matter. Other means have been proposed and tried with more or less success.

Another shortcoming of the quenching method consists in the metastable character of the pentasulfide produced, since its reactivity tends to decrease in storage or on contact with solvent vapors, or even in response to a temperature rise.

Furthermore, the quenching method requires a phosphorus pentasulfide user, who at times needs a high reactivity $P_2S_5$ and at other times a lower reactivity $P_2S_5$, depending on the alcohol or phenol which he may be using, to stock at least two different types to meet his requirements.

One way to avoid these disadvantages, is to increase the speed of reaction of the phosphorus pentasulfide by the use of catalysts. Whereas the quenching process increases the over-all reaction speed by modifying the structure of the $P_2S_5$, the catalytic process apparently leaves this unchanged and acts on the reaction speed of the dissolved $P_2S_5$, or in other words increases the value of the reaction constant $k$.

Unfortunately, the catalysts proposed up to now are few in number and not very effective unless used in excessive amounts.

U.K. Pat. No. 1,228,528 claims, for example, to employ traces of ammonia to catalyze the reaction of $P_2S_5$ with alcohols and phenols.

P. Bencze (cited above) uses potassium phenate in a molar dose of 0.3% to activate the phenolysis of phosphorus pentasulfide.

N. I. Zemlyanskii and L. V. Glushkova (Zhurnal Obshchei Khimii 37(4) (1967), 775–777) react $P_2S_5$ with 2,4-dichlorophenol and with 2,4,6-trichlorophenol in the presence of a massive quantity of triethylamine (2 mols to 1 of $P_2S_5$).

N. I. Zemlyanskii and I. V. Murav'ev (Doklady Akademii Nauk SSR 163, 1965, No. 3, 654–655) likewise use large amounts of triethylamine or potash to catalyze the reaction of $P_2S_5$ with methyl and hexyl alcohols, phenol and p-nitrophenol.

Kalashnikov, V. P. (Zhurnal Obshchei Khimii 40 (1970), No. 9, 1954–1966), following the preceding method, react phosphorus pentasulfide with pyrocatechol in the presence of a stoichiometric quantity of triethylamine.

Lastly, M. G. Imaev, I. V. Tikunova and I. S. Akhmetzhanov (USSR Pat. No. 285,146) describe the reaction of $P_2S_5$ with a $C_4$ to $C_9$ alcohol in the presence of azo-bis-isobutyronitrile.

SUMMARY OF THE INVENTION

The novel catalysts of the present invention have the advantage, over known catalysts, of being generally far more effective in small amounts.

These new catalysts belong to the group consisting of:

(A) Nitrogen derivatives that may be represented by the formula

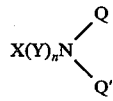

III having a total of 1 to 20 carbon atoms and 1 to 10 heteroatoms of O, S, N or P, in which X, Q and Q' may or may not be alike and each represent hydrogen or a univalent hydrocarbon radical, or form rings when taken together two-by-two, and/or are substituted by oxygen, sulfur and/or nitrogen, the latter not being involved in the N—Q, N—Q' and X—Y bondings; Y represents oxygen, sulfur, a monosubstituted nitrogen atom or a mono- or disubstituted phosphorus atom; and the value of $n$ is 0 or 1.

(B) Nitrogen derivatives represented by the formula $$(X')_m(Y)_n N=Z \quad\quad IV$$

having a total of 0 to 20 carbon atoms, and 1 to 10 heteroatoms of O, S, N or P, in which $m$ is 0 or 1, X' has the same meaning as X given above or is equivalent to —N=Z or —NQQ', and Z represents oxygen, sulfur or a bivalent hydrocarbon or carbon radical, which may form a ring with X' and/or be substituted with oxygen, sulfur and/or nitrogen; Y, $n$, Q and Q' have the same meanings as in (A) above.

(C) Nitrile derivatives that may be represented by the formula $$X(Y)_n-C\equiv N \quad\quad V$$

having a total of 1 to 20 carbon atoms and 1 to 6 heteroatoms of O, S, N or P, in which X, Y and $n$ have the same meanings as under (A) above.

The expression "may be represented by the formula . . ." as used in defining (A), (B) and (C) means that if the compound in question has several mesoisomeric of tautomeric structures, at least one of them can be represented by the formula given.

This invention also relates to combinations of several of the catalysts defined above in A, B or C above, as well as their salts with organic or mineral acids or bases.

DESCRIPTION OF THE PREFERRED EMBODIMENTS

Examples of the catalysts disclosed above are as follows:

(1) Simple amines, primary secondary or tertiary, aliphatic, aromatic or mixed arylaliphatic, such as methylamine, ethylamine, isopropylamine, butylamine, dimethylamine, diethylamine, triethylamine, ethanolamine, ethylenediamine, morpholine, enamines, aniline, dimethylaniline, p-toluidine, o-pheylenediamine, o-aminophenol, anthranilic acid and its derivatives, pyrrole, phenothiazine.

(2) Amides or imides of carboxylic acids, such as formamide, acetamide, acrylamide, dimethylformamide, dimethylacetamide, N-methylpyrrolidone, succinimide, urea, methylureas, ethylene urea, biuret, glycoluril, urethanes, ammonium carbamate.

(3) Amides of thiocarboxylic acids, such as thioacetamide, thiobenzamide, N,N-dimethylthioformamide, thiourea, N-methylthiourea, N-ethylthiourea, sym. dibutylthiourea, ethylenethiourea.

(4) Compounds containing the N—O link, such as hydroxylamine, methylhydroxylamines, oxaziranes, aldoximes, ketoximes, quinone-oximes, hydroxamic acids, amidoximes, O-substituted oximes, nitrolic acids, isoxazole and its derivatives, isonitrososomalonylguanidine.

(5) Compounds containing the N-N link, such as hydrazine, methylhydrazine, N-N-dimethylhydrazine, phenylhydrazine, aminoquanidine, semicarbazide, the hydrazones, azines, derivatives of pyrazole, indazole and pyrazoline, nitrosamines, benzotriazole, 4-amino-1,2,4-triazole, 4-aminoantipyridine, hydrazoic acid and its derivatives.

(6) Compounds containing the N-S link, such as sulfamic acid, sulfinamides, sulfonamides, saccharine, benzothiadiazole-2,1,3.

(7) Compounds containing the N-P link, such as amides of phosphorous, phosphoric and thiophosphoric acids.

(8) Schiff bases.

(9) Pyridic bases, such as pyridine, methylpyridines, vinylpyridines, quinoline, isoquinoline, acridine, $\alpha,\alpha'$-dipyridyl, 2- and 3-hydroxypyridines, 8-hydroxyquinoline, 2-aminopyridines, quinidine.

(10) Derivatives of pyrazine, pyrimidine, pyridazine or 1,3,5-triazine.

(11) Compounds having the

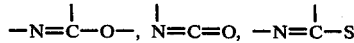

or —N=C=S link, such as derivatives of oxazole, oxazoline or oxazine, iminoethers, derivatives of isourea of isothiourea, isocyanates, isothiocyanates, mercaptobenzothiazole.

(12) Amidines carbodiimides and compounds containing the

or —N=C=N— link, such as guanidine, derivatives of imidazole or imidazoline.

(13) Nitrogen compounds such as oxides of nitrogen, nitrous acid, nitrites, pseudonitrols, nitrosophenols.

(14) Nitriles such as hydrocyanic acid, acetonitrile, acrylonitrile, benzonitrile, cyanamide and its salts, dicyanodiamide salts and esters of cyanic and thiocyanic acids.

The amount of catalyst to be used may range from 0.01 to 10% by weight of the alcohol or phenol, the preferred range, however, being between 0.1 and 2% of the latter.

The catalysts of this invention may be employed in a variety of ways. They may be dissolved or suspended beforehand in the whole or a part of the alcohol or phenol reagent; alternatively, particularly when the catalyst is a solid, they may be mixed with the $P_2S_5$ powder; they may be added to the $P_2S_5$ plus alcohol or phenol mixture, at one time or in smaller aliquots; they may be used in the pure state or in solution in a suitable solvent; in some cases, they may even be prepared in situ, as for example the urethanes, which may be obtained fresh by adding a calculated quantity of isocyanate to the alcohol or phenol which one intends to react with the phosphorus sulfide:

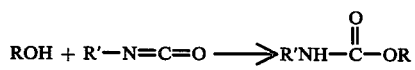    VI

Some of these catalysts when used in too small a quantity have a negative effect which effect becomes positive when the catalyst is present in larger quantities (See Examples 22 and 23 below). In addition, some of these catalysts only manifest a positive effect after a latent period of several minutes, during which time they act as inhibitors. (See Example 152 below).

This invention may be illustrated by, although not limited to, Examples 1 to 160 below.

In the Examples which follow, the activities of each catalyst has been assessed by the following simplified test.

The measured amount of catalyst (usually 0.5 g in the case of a solid or 0.5 ml in the case of a liquid) was dissolved in 100 ± 0.1 g of the alcohol or phenol selected to be reacted in a 250-ml beaker having a glass cover pierced to admit a 1/10-° thermometer and provided with good heat insulation. With the beaker under agitation by a magnetic agitator and the temperature of the liquid close to room temperature (about 22° C.) or, in the case of cyclohexanol and tert.-butanol, slightly above the melting point of the alcohol, 10 ± 0.01 g. of powdered $P_2S_5$ was introduced at one time. The temperature was recorded every minute.

At the end of 15 minutes, an equal amount of fresh catalyst was added, and any temperature variation of $\Delta't$ occurring immediately after this second addition was measured. This difference in temperature was generally due to the heat of neutralization of the catalyst, when basic, by the acid $(RO)_2PS_2H$.

The speed of reaction was determined empirically from the value of $\Delta t$ measured at the end of 7 minutes (or in exceptional cases 15 minutes), after correcting for the heat of neutralization $\Delta't$ defined in the preceding paragraph. In each instance, this was compared with the value $\Delta t_O$ provided by a control with no catalyst.

It will be noted that owing to unavoidable calory losses, this simplified test tends to underrate the most effective catalysts.

All the tests were carried out on three different lots of phosphorus pentasulfide, respectively identified as L, T and C, the former two being of recent manufacture and the last having a storage age of three years, their granulometries are given below:

Cumulative retention (%) on screen of mesh opening:

|  | 0.315 | 0.200 | 0.125 | 0.080 | 0.040 mm |
|---|---|---|---|---|---|
| Pentasulfide L | 1.25 | 3.80 | 13.30 | 41.40 | 83.50 |
| Pentasulfide T | 22.25 | 43.10 | 56.86 | 76.10 | 89.80 |
| Pentasulfide C | 2.04 | 5.75 | 11.80 | 21.50 | 67.45 |

EXAMPLES 1 TO 160

TABLE I

ISOPROPANOL + PENTASULFIDE C

| Ex. No. | Catalyst | | $\Delta t$, ° C. in 7 min. |
|---|---|---|---|
| Control | None | | 2.0 |
| 1 | Monomethylurea | 0.2 g | 4.0 |
| 2 | Monomethylurea | 0.5 g | 6.7 |
| 3 | Monomethylurea | 1.0 g | 8.1 |
| 4 | Monomethylurea | 2.0 g | 10.1 |
| 5 | Monomethylurea | 5.0 g | 12.8 |
| 6 | Urea | 0.5 g | 7.3 |
| 7 | N,N'-dimethylurea | 0.5 g | 4.8 |
| 8 | Trimethylurea | 0.5 ml | 4.2 |
| 9 | Tetamethylurea | 0.5 ml | 4.0 |
| 10 | Biuret $H_2N\ CO-NH-CO-NH_2$ | 0.5 g | 3.6 |
| 11 | Formamide | 0.5 ml | 3.3 |
| 12 | Succinimide 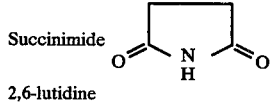 | 0.5 g | 3.5 |
| 13 | 2,6-lutidine | 0.5 ml | 2.8 |
| 14 | Saccharine (i.s) 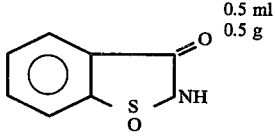 | 0.5 g | 4.0 |
| 15 | Acetoguanamine | 0.5 g | 2.7 |
| 16 | Sodium nitrite | 0.5 g | 5.2 |
| 17 | Methyl anthranilate | 0.5 ml | 3.9 |
| 18 | Anthranylamide | 0.5 g | 3.2 | i.s = Incompletely soluble

TABLE II

ISOPROPANOL + PENTASULFIDE L

| Example No. | Catalyst | | Δt, °C. in 7 min. |
|---|---|---|---|
| Control | None | | 3.8 |
| 19 | Imidazole | 1 g | 10.4 |
| 20 | Pyridine | 1 ml. | 4.4 |
| 21 | Methyl-2-ethyl-5-pyridine | 1 ml | 6.1 |
| 22 | Triethylamine | 0.1 ml | 1.5 |
| 23 | Triethylamine | 1 ml | 4.6 |
| 24 | Ammonium carbamate | 0.5 g | 6.6 |
| 25 | Formamide oxime HC=NOH (NH$_2$) | 0.5 g | 8.4 |
| 26 | Sarcosine CH$_3$NH—CH$_2$COOH | 0.5 g | 5.0 |
| 27 | Ethylenethiourea | 0.5 g | 4.6 |

TABLE III

ISOPROPANOL + PENTASULFIDE T

| Example No. | Catalyst | | Δt, °C. in 7 min. |
|---|---|---|---|
| Control | None | | 3.1 |
| 28 | Maleic hydrazide (i.s) | 0.5 g | 3.9 |
| 29 | Pyrazole (i.s) | 0.5 g | 7.0 |
| 30 | Imidazole | 1 g | 8.0 |
| 31 | Diacetyl monoxime O=C(Me)—C(Me)=NOH | 0.5 g | 3.4 |
| 32 | Ammonium sulfamate | 0.5 g | 5.4 |
| 33 | Hydroxylamine hydrochloride | 0.5 g | 4.3 |
| 34 | Urea | 0.5 g | 6.6 |
| 35 | Sodium cyanate | 0.5 g | 3.7 |
| 36 | Potassium thiocyanate | 0.5 g | 5.1 |
| 37 | Aminoguanidine (bicarbonate) H$_2$N—NH—C(=NH)—NH$_2$ | 0.5 g | 5.0 |
| 38 | 4-amino-1,2,4-triazole | 0.5 g | 4.0 |

(i.s) = Incompletely soluble

TABLE IV

ISODECANOL OXO + PENTASULFIDE L

| Ex. No. | Catalyst | | Δt, °C. in 7 min. |
|---|---|---|---|
| Control | None | | 2.4 |
| 39 | Ortho-Phenylenediamine | 0.5 g | 3.2 |
| 40 | Acetaldoxime CH$_3$CH=NOH | 0.5 ml | 3.9 |
| 41 | Acetoxime Me$_2$C=NOH | 0.5 g | 5.9 |
| 42 | Cyclohexanone-oxime C$_6$H$_{10}$=NOH | 0.5 g | 3.8 |
| 43 | Oxazole | 0.5 ml | 3.8 |
| 44 | Methyl-2 oxazoline | 0.5 ml | 4.9 |
| 45 | Phenylhydrazine | 0.5 ml | 2.6 |
| 46 | Isobutylalcyclohexalimine Me$_2$C—CH=N—C$_6$H$_{11}$ | 0.5 ml | 4.1 |
| 47 | 2-Nitroso-2-nitro-propane Me$_2$C(NO$_2$)(NO) | 0.5 g | 8.6 |
| 48 | Propane nitrolic acid Et—C(NO$_2$)=NOH | 0.5 g | 4.4 |
| 49 | N,N'-dibutylthiourea | 0.5 g | 2.6 |

TABLE V

ISODECANOL OXO + PENTASULFIDE T

| Example No. | Catalyst | | Δt, °C. in 7 min. |
|---|---|---|---|
| Control | None | | 2.0 |
| 50 | Butanone-oxime Et MeC—NOH | 0.5 ml | 2.4 |
| 51 | N-Nitroso diethylamine Et₂N—N=O | 0.5 ml | 2.2 |
| 52 | 3,5-dinitrobenzoic acid (*) | 0.5 g | 2.4 |

*Reduced to nitroso compound by H₂S liberated during the reaction.

TABLE VI

CYCLOHEXANOL + PENTASULFIDE L

| Example No. | Catalyst | | Δt, °C. in 7 min. |
|---|---|---|---|
| Control | None | | 6.2 |
| 53 | | 0.5 g | 10.2 |

TABLE VI-continued

CYCLOHEXANOL + PENTASULFIDE L

| Example No. | Catalyst | | Δt, °C. in 7 min. |
|---|---|---|---|
| 54 | Dimethylformamide | 0.5 ml | 7.4 |

TABLE VII

CYCLOHEXANOL + PENTASULFIDE T

| Example No. | Catalyst | | Δt, °C. in 7 min. |
|---|---|---|---|
| Control | None | | 2.5 |
| 55 | Ortho-Aminophenol | 0.5 g | 4.4 |
| 56 | Acetamide | 0.5 g | 3.0 |
| 57 | Acrylamide | 0.5 g | 3.4 |
| 58 | Ethylene urea 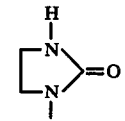 | 0.5 g | 5.6 |
| 59 | Acetohydroxamic acid CH₃—CO—NHOH | 0.5 g | 4.8 |
| 60 | Indazolone 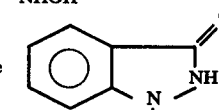 | 0.5 g | 3.4 |
| 61 | 2-aminothiazole 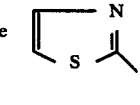 | 0.5 g | 4.4 |
| 62 | 3,5-dimethylpyrazole 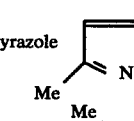 | 0.5 g | 5.4 |
| 63 | 4,6-dimethyl-2-mercaptopyrimidine 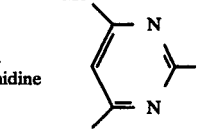 | 0.5 g | 4.2 |
| 64 | 6-amino-2,4-dimethylpyrimidine 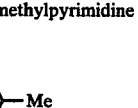 | 0.5 g | 3.5 |
| | 8-hydroxyquinoline 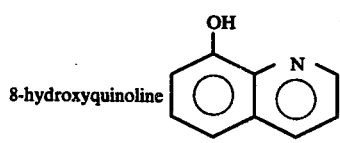 | | |

TABLE VIII

CYCLOHEXANOL + PENTASULFIDE C

| Example No. | Catalyst | Δt, °C. in 7 min. |
|---|---|---|
| 1st. Control | None | 4.7 |

TABLE VIII-continued
CYCLOHEXANOL + PENTASULFIDE C

| Example No. | Catalyst | | Δt, °C. in 7 min. |
|---|---|---|---|
| 65 | 2,4-lutidine | 0.5 ml | 11.5 |
| 66 | 2,4,6-collidine  Me—[pyridine with Me at 2,4,6]—Me | 0.5 ml | 8.4 |
| 67 | 2-ethylimidazole [imidazole-NH, Et] | 0.5 g | 9.9 |
| 68 | N-Ethyl imidazole [imidazole N—Et] | 0.5 ml | 9.5 |
| 69 | 2,5-dimethylpyrrole  Me—[pyrrole-NH]—Me | 0.5 ml | 5.2 |
| 70 | Tetramethylurea | 0.5 ml | 5.2 |
| 71 | o-(2-cyanoethyl)-butanoneoxime  Et Me C=N—O—CH$_2$CH$_2$CN | 0.5 ml | 5.2 |
| 72 | Ethyl N-phenyl formimidate  HC(OEt)=NPh | 0.5 | 5.4 |
| 73 | 2-aminopyrimidine [pyrimidine—NH$_2$] | 0.5 g | 6.0 |
| 74 | Benzothiadiazole-2,1,3 [benzothiadiazole structure] | 0.5 g | 5.6 |
| 75 | Benzoguanamine  Ph—[pyrimidine with 2 NH$_2$] | 0.5 g | 5.7 |
| 76 | Phosphorous trimorpholide | 0.5 g | 7.4 |
| 2nd Control (*) | None | | 4.1 |
| 77 | N-N-dimethylbenzene sulfonamide  Ph—SO$_2$N Me | 0.5 g | 5.2 |
| 78 | Thiophosphoric tripiperidide  (H N—[piperidine])$_3$—PS | 0.5 g | 4.8 |

(*) Cyclohexanol of different origin, less pure

TABLE IX
TERTIARY BUTANOL

| Example No. | PENTA SULFIDE | Catalyst | | t, °C. in 15 min. |
|---|---|---|---|---|
| Control | L | None | | 0.4 |
| 79 | L | α-picoline | 0.5 ml | 3.5 |
| Control | T | None | | 0.2 |
| 80 | T | Acrylamide | 0.5 g | 1.1 |
| Control | C | None | | 0.5 |
| 8 | C | 2,4-lutidine | 0.5 ml | 1.7 |
| 82 | C | 2-ethylimidazole [imidazole-NH, Et] | 0.5 g | 2.0 |

TABLE X
XYLENOL + PENTASULFIDE L

| Example No. | Catalyst | | Δt, °C. in 7 min. | in 15 min. |
|---|---|---|---|---|
| Control | None | | 0. g | 1.6 |
| 83 | Dicyanodiamide | 0.5 g | 1.5 | 2.4 |
| 84 | Acetoxime | 0.5 g | 1.8 | 2.8 |
| 85 | Acetohydroxamic acid  CH$_3$—CO—NHOH | (i.s.) 0.5 g | 7.4 | 6.4 |
| 86 | Hydrazine (hydrate) | 0.5 ml | 1.6 | 2.7 |
| 87 | 2-nitroso-2-nitropropane | 0.5 g | 2.0 | 2.6 |
| 88 | Potassium cyanide | 0.5 g | 1.8 | 2.0 | i.s. = Incompletely soluble

TABLE XI

XYLENOL + PENTASULFIDE C

| Example No. | Catalyst | | Δt, °C. in 7 min. | Δt, °C. in 15 min. |
|---|---|---|---|---|
| 1st Control | None | | 0.4 | 0.9 |
| 89 | α-picoline | 0.5 ml | 0.4 | 1.3 |
| 90 | Pyrazole (structure: ring with N-NH) | 0.5 g | 1.4 | 1.8 |
| 91 | 2-Ethylimidazole (structure with Et) | 0.5 g | 1.7 | 2.2 |
| 92 | Formamide oxime $HC(NH_2) = NOH$ | 0.5 g | 1.6 | 2.0 |
| 93 | Phosphorous trimorpholide $(O\text{-morpholine-}N)_3P$ | 0.5 g | 2.7 | 3.5 |
| 2nd Control (*) | None | | 0.1 | 0.3 |
| 94 | Imadazole | 0.5 g | 0.6 | 0.8 |
| 95 | 2-hydroxypyridine | 0.5 ml | 0.9 | 1.7 |
| 96 | Succinimide | 0.5 g | 0.3 | 0.6 |
| 97 | 2-nitroso-2-nitropropane | 0.3 g | 0.6 | 1.1 |
| 98 | Dinitrosopentamethylene tetramine (ON—N...N—NO structure) | 0.5 g | 2.0 | 2.1 |

(*) Xylenol from a different source

TABLE XI

GLYCOL + PENTASULFIDE C

| Example No. | Catalyst | | Δt, °C. in 7 min. | Δt, °C. in 15 min. |
|---|---|---|---|---|
| Control | None | | 2.0 | 2.8 |
| 99 | Monomethylurea | 0.5 g | 2.7 | 3.9 |
| 100 | N,N'-Dimethylurea | 0.5 g | 2.5 | 3.6 |
| 101 | Sulfate of bis(S-Methyl isothiouronium) $(H_2N-\overset{SMe}{C}=NH)_2,H_2SO_4$ + Triethylamine | 0.5 g / 0.5 ml | 2.6 | 3.9 |
| 102 | Glycol-urile (bicyclic structure with N-H and C=O) | 0.5 g | 2.2 | 2.9 |
| 103 | γ-Picoline | 0.5 ml | 2.2 | 3.1 |
| 104 | Potassium cyanide | 0.5 g | 2.3 | 3.1 |
| 105 | Sodium cyanate | 0.5 g | 4.2 | 6.0 |
| 106 | Methyl isocyanate* | 0.5 ml | 2.3 | 3.1 |
| 107 | L-Histidine ($HOOC-CH(NH_2)-CH_2-$imidazole) | 0.5 g | 2.7 | 2.9 |
| 108 | Uric Acid + Triethylamine | 0.5 g / 0.5 ml | 2.7 | 2.9 |
| 109 | Semicarbazide(hydrochloride) $H_2N-CO-NH-NH_2$ | 0.5 g | 2.1 | 2.9 |
| 110 | Sodium nitrite** | 0.5 g | 3.8 | 3.7 |
| 111 | Dinitroso pentamethylene tetramine | 0.5 g | 5.3 | 5.1 |

TABLE XI-continued

GLYCOL + PENTASULFIDE C

| Example No. | Catalyst | | Δt, °C. in 7 min. | Δt, °C. in 15 min. |
|---|---|---|---|---|
| 112 | Isonitroso malonylguanidine (ON—N, N—NO piperazine structure) | 0.5 g | 2.6 | 3.8 |
|  |  | 0.5 | 2.6 | 3.8 |
| 113 | Imidazole | 0.5 g | 4.0 | 5.4 |
| 114 | α-Picoline | 0.5 ml | 2.4 | 3.2 |
| 115 | Formamide oxime HC(NH$_2$)=NOH | 0.5 g | 4.0 | 4.6 |
| 116 | Guanidine (carbonate) (H$_2$N)$_2$ C=NH | 0.5 g | 2.7 | 3.3 |
| 117 | Sodium azide NaN$_3$ | 0.5 g | 3.9 | 5.2 |

*Evidently reacts with glycol to form an N-methylurethane
**Reaction in nitrogen atmosphere to avoid H$_2$S-sulfur oxidation catalyzed by oxides of nitrogen formed from nitrite.

TABLE XIII

2-BUTOXYETHANOL + PENTASULFIDE L

| Example No. | Catalyst | | Δt, °C. in 7 min |
|---|---|---|---|
| Control | None |  | 4.3 |
| 118 | α-Picoline | 0.5 ml | 15.8 |
| 119 | 2,6-lutidine | 0.5 ml | 12.4 |
| 120 | 2-hydroxypyridine | 0.5 g | 13.7 |
| 121 | Guanidine (carbonate) | 0.5 g | 11.7 |
| 122 | N-methyl pyrrolidone |  |  |
| 123 | Urea nitrate | 0.5 g | 12.1 |
| 124 | 2,4,5-trimethyloxazole | 0.5 ml | 15.6 |
| 125 | Trimethyl-3,5-5 pyrazoline-2 (hydrochloride) / Triethylamine | 0.5 g / 0.5 ml | 12.8 |
| 125 | Dimethylglyoxime HON=C(Me)—C(Me)=NOH |  | 6.0 |
| 127 | Sodium nitrite (i.s) [with 1-nitroso-2-naphthol structure] | 0.5 g | 18.0 |
| 128 | α-Nitroso β naphtol | 0.5 g | 9.4 |
| 129 | Picric acid(*) O$_2$N—C$_6$H$_2$(OH)(NO$_2$)$_2$ | 0.5 g | 5.6 |
| 130 | 2-mercaptobenzothiazole | 0.5 g | 5.4 |

(*) Reduced by H$_2$S to nitroso compound
(i.s) = Incompletely soluble

TABLE XIV

2-BUTOXYETHANOL + PENTSULFIDE T

| Example No. | Catalyst | | Δt, °C. in 7 min. |
|---|---|---|---|
| Control | None | | 4.1 |
| 131 | N-Methylmorpholine | 0.5 ml | 6.9 |
| 132 | Dimethylacetamide | 0.5 ml | 9.1 |
| 133 | Lysidine (structure: ring with NH, N, Me) | 0.5 g | 10.3 |
| 134 | Dicyandiamide | 0.5 g | 9.1 |
| 135 | 5-Ethyloxazole (Et—⟨O,N⟩) | 0.5 ml | 12.1 |
| 136 | α-Picoline | 0.5 ml | 11.2 |
| 137 | 2-methylpyrazine (Me on pyrazine) | 0.5 ml | 10.3 |
| 138 | Hydrazine hydrate | 0.5 ml | 9.7 |
| 139 | Acetone-azine Me$_2$C=N—N=CMe$_2$ | 0.5 ml | 9.4 |
| 140 | Cyclohexanone phenylhydrazone C$_6$H$_{10}$=N—NHPh | 0.5 g | 7.2 |
| 141 | Benzotriazole | 0.5 g | 7.1 |
| 142 | 4-Aminoantipyrine (H$_2$N-, Me, N, N-Ph, Me, =O) | 0.5 g | 4.9 |
| 143 | N-Cyclohexyl isopropyl oxazirane Me$_2$CH—CH—N—C$_6$H$_{11}$ (with O bridge) | 0.5 ml | 5.1 |
| 144 | 2,4-dinitroso-1,3-dihyroxybenzene (HO, NO, ON, OH on benzene) | 0.5 g | 8.5 |
| 145 | Thiourea | 0.5 g | 9.4 |
| 146 | Phenothiazine | 0.5 g | 5.0 |

TABLE XV

2-BUTOXYETHANOL + PENTASULFIDE C

| Example No. | Catalyst | | Δt, °C. in 7 min. | Δt, °C. in 15 min. |
|---|---|---|---|---|
| Control | None {normal / understream of N} | | 6.9 / 6.9 | 11.8 |
| 147 | Sodium nitrite (under nitrogen)(i.s.) | 0.5 g | 16.1 | |
| 148 | Butylamine | 0.5 ml | 14.3 | |
| 149 | Diethylamine | 0.5 ml | 13.7 | |
| 150 | Ethylenediamine | 0.5 ml | 13.5 | |
| 151 | Succinimide | 0.5 g | 7.0 | |
| 152 | Quinidine (*) | 0.5 g | 3.1 | 14.0 |
| 153 | γ-Picoline | 0.5 ml | 15.5 | |
| 154 | Quinoline | 0.5 ml | 14.2 | |
| 155 | Isoquinoline | 0.5 ml | 9.6 | |

TABLE XV-continued

2-BUTOXYETHANOL + PENTASULFIDE C

| Example No. | Catalyst | | Δt, °C. | |
|---|---|---|---|---|
| | | | in 7 min. | in 15 min. |
| 156 | 3-Hydroxypyridine | 0.5 g | 15.2 | |
| 157 | 2-Aminopyridine | 0.5 g | 14.4 | |
| 158 | 2-Amino-4-methylpyridine | 0.5 g | 15.0 | |
| 159 | 2-Amino-6-methylpyridine | 0.5 g | 15.1 | |
| 160 | Ethyl β-aminorotonate $\text{CH}_3-\underset{\underset{\text{NH}_2}{|}}{\text{C}}=\text{CH}-\text{COOEt}$ | 0.5 ml | 13.1 | |
| (*) | Of the following structure: | | | |

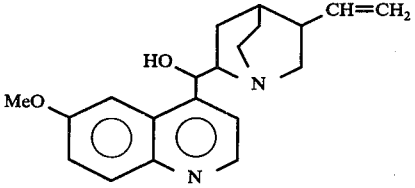

EXAMPLES 161 to 171

In the following examples, a fourth type of pentasulfide, identified as D, was used, which was freshly prepared and had the following granulometry:

| Mesh opening | 0.315 | 0.200 | 0.125 | 0.080 | 0.040 mm |
|---|---|---|---|---|---|
| Cumulative retention | 6.5 | 16.05 | 29.8 | 45.85 | 73.5 % |

The tests were carried out in accordance with the following procedure.

A ground triple-necked flat-bottom flask A was immersed in a bath thermostatically controlled at 40° ± 0.2° C. 10 + 0.05 g $P_2S_5$ (for 45 mmols) and a bar magnet, were placed into A.

Two of the three openings on the flask were fitted with a dry nitrogen supply line and a reflux condenser fed with brine at −10° C, respectively. At the third opening a mixture of 7.9 ml of methanol, representing a 10% excess over the quantity theoretically required by Formula (I), and 15 ml dichloroethane, was introduced. If the catalyst was solid, it was placed in A with the phosphorus pentasulfide; if it was liquid, it was dissolved in the methanoldichloroethane mixture.

Immediately after adding the last reagents, the third opening in the flask was sealed with a ground glass stopper, nitrogen circulation regulated at a flow of 200 ml/min., was commenced and magnetic agitation was initiated.

The gases leaving the condenser passed through a safety bottle and were absorbed in a wash bottle F containing 250 ml 0.5N aqueous soda.

Every quarter of an hour, a 5-ml aliquot sample was taken from F and titrated for sulfides by iodimetry.

The test ordinarily took an hour, but was stopped sooner if the conversion of the pentasulfide occurred sooner.

Table XVI presents the results obtained.

TABLE XVI

| Example | Catalyst | | $H_2S$ Evolved (% of theoretical)* | | | | Remarks |
|---|---|---|---|---|---|---|---|
| | | | 15 min. | 30 min. | 45 min. | 1 hr. | |
| Control | None | | | 43.9 | 84.8 | 93.4 | 95.5 | Some $P_2S_5$ was left undissolved after 2 hrs. of reaction |
| 161 | α-picoline | 0.1 ml | 69.5 | 105.8 | — | — | $P_2S_5$ entirely dissolved after 25 min. |
| 162 | Hydrazine hydrate | 0.1 ml | 66.6 | 90.0 | 97.8 | 98.5 | $P_2S_5$ entirely dissolved after 1 hr. 15 min. ($H_2S$ 99% of theoretical) |
| 163 | Urea | 0.1 g | 82.4 | 105.6 | 107.8 | — | |
| 164 | Sodium nitrite | 0.1 g | 64.8 | 89 | 96 | 96.8 | $P_2S_5$ dissolved after 55 min.** |
| 165 | Imidazole | 0.1 g | 89.4 | 103.3 | — | — | |
| 166 | Acetohydroxamic acid | 0.1 g | 70.4 | 96.9 | 102 | 105.7 | |
| 167 | Diethylamine | 0.1 ml | 74.8 | 102.2 | 106.8 | — | |
| 168 | Dinitrospentamethylenetetramine | 0.1 g | 68.9 | 94.5 | 101.1 | 101.1 | |
| 169 | Sodium cyanate | 0.1 g | 59.7 | 92.2 | 102.2 | — | |
| 170 | Sodium azide | 0.1 g | 75.7 | 101.8 | 107.9 | — | |
| 171 | PAM*** | 0.1 g | 80 | 106.2 | 110 | — | |

Notes to Table XVI

*In most tests, more $H_2S$ was collected at end of reaction than predicted theoretically; this is because, as previously mentioned, Formula I is only an approximation.

**The solution in the $H_2S$ absorber assumed a yellow coloration during the first few minutes; this is probably due to the formation of sodium polysulfides through oxidation of $H_2S$ by oxides of nitrogen. By the same token, the quantity of $H_2S$ found by analysis here is less than the theoretical.

***Abbreviation for 2-pyridine aldoxime methiodide, formula:

TABLE XVI-continued

| Example | Catalyst | H₂S Evolved (% of theoretical)* 15 min. 30 min. 45 min. 1 hr. | Remarks |
|---------|----------|----|----|

$$\left[ \begin{array}{c} \text{pyridinium ring with } N^{\oplus}\text{-Me and CH=N-OH substituent} \end{array} \right] I^{\ominus}$$

I claim:

1. A process for accelerating the alcoholysis or phenolysis of phosphorus pentasulfide which comprises contacting the phosphorus pentasulfide with an alcohol or phenol in the presence of a nitrogen-containing catalyst in amount from 0.01 to 10% by weight of the alcohol or phenol, the molecule of said catalyst having not more than 14 carbon atoms or more than 4 nitrogen atoms or more than 4 heteroatoms selected from the group consisting of oxygen, sulfur and phosphorus, said catalyst being (a) an amide or imide of a carboxylic acid, such as N-methylpyrrolidone, urea, a methylurea, ethylene urea, biuret, glycolurile, urethane or ammonium carbamate; or an amide of thiocarboxylic acid such as N,N dimethyl-thioformamide, thiourea, N-methylthiourea, N-ethylthiourea, sym. dibutyl thiourea of ethylene thiourea; or (b) a compound having a N-O link, being a nitrogen oxide or nitrous acid or metal nitrite or 2-nitroso-2-nitro propane or propane nitrolic acid; or hydroxylamine or a methyl hydroxylamine, oxazirane, an aldoxime or ketoxime of a carbonyl compound having up to 14 carbon atoms, a quinone-oxime, hydroxamic acid, isoxazole or isonitrosomalonyl guanidine; or (c) a compound having a N-N link, being azine, hydrazine, methyl hydrazine, N,N-dimethyl hydrazine, phenyl hydrazine, amino guanidine, semi-carbazide, pyrazole, indazole, pyrazoline, bensotriazole, 4-amino-1,2,4 triazole, 4-amino antipyridine or hydrazoic acid; or (d) compounds having a N-P link, being the amides of phosphorous, phosphoric or thiophosphoric acids; or (e) quinidine; or pyridine or quinoline bases carrying hydroxyl or amino groups on the ring, being 2-hydroxypyridine, 3-hydroxypyridine, 8-hydroxyquinoline, or 2-amino pyridine; or (f) compounds having a —N=C—O—, N=C=O, —N=C—S or —N=C=S link, being oxazole or oxazoline, oxazine, isourea, isothiourea, metal cyanate or thiocyanate, mercaptobenzothiazole, N,N'-dibutylthiourea or methyl-2-oxazoline; or (g) guanidine, or imidazole, or imidazoline; or (h) cyanamide, or dicyanodiamide or the esters of cyanic or thiocyanic acid.

2. The process according to claim 1, wherein the quantity of catalyst by weight is between 0.1 and 2% of the alcohol or phenol.

* * * * *

UNITED STATES PATENT AND TRADEMARK OFFICE
CERTIFICATE OF CORRECTION

PATENT NO. : 4,083,899
DATED : April 11, 1978 (Page 1 of 2)
INVENTOR(S) : Michel Demarcq It is certified that error appears in the above-identified patent and that said Letters Patent are hereby corrected as shown below:

Column 6, line 47, reads "Tetamethylurea", should read
--Tetramethylurea--

Column 9, Table VI, Example No. 53. The catalyst and diagram for this Example appears at bottom of Column 9.

Column 11, Example No. 71, reads "5.2", should read --5.4--

Example No. 72, reads "0.5", should read --0.5 ml--

Example No. 77, reads "Ph-SO$_2$N Me", should read
--Ph-SO$_2$N Me$_2$--

Column 11, Table IX, heading reads "t,°C", should read
--$\Delta$t,°C--

Example reads "8", should read --81--

UNITED STATES PATENT AND TRADEMARK OFFICE
CERTIFICATE OF CORRECTION

PATENT NO. : 4,083,899                       (Page 2 of 2)
DATED : April 11, 1978
INVENTOR(S) : Michel Demarcq It is certified that error appears in the above–identified patent and that said Letters Patent are hereby corrected as shown below:

Column 13, second Table, reads "Table XI", should read
--Table XII--

Column 15, first line, reads "Table XI-continued", should read
--Table XII-continued--

Column 15, Table XIII, Example 125, second occurrence, should read --126--

Column 17, Table XV, Control reads "6.9", should read
--6.8--

Column 19, line 36, reads "(for 45 mmols)" should read
--(or 45 mmols)--

Signed and Sealed this

Thirty-first Day of October 1978

[SEAL]

Attest:

RUTH C. MASON
Attesting Officer

DONALD W. BANNER
Commissioner of Patents and Trademarks